United States Patent
Zhou et al.

(10) Patent No.: US 9,766,182 B2
(45) Date of Patent: Sep. 19, 2017

(54) LASER INDUCED BREAKDOWN SPECTROSCOPY (LIBS) APPARATUS WITH DUAL CCD SPECTROMETER

(71) Applicants: Xin Jack Zhou, Hockessin, DE (US); Sean Xiaolu Wang, Wilmington, DE (US); Qun Li, Newark, DE (US)

(72) Inventors: Xin Jack Zhou, Hockessin, DE (US); Sean Xiaolu Wang, Wilmington, DE (US); Qun Li, Newark, DE (US)

(73) Assignee: BWT Property, Inc., Newark, DE (US)

( * ) Notice: Subject to any disclaimer, the term of this patent is extended or adjusted under 35 U.S.C. 154(b) by 84 days.

(21) Appl. No.: 14/708,638

(22) Filed: May 11, 2015

(65) Prior Publication Data

US 2016/0334335 A1    Nov. 17, 2016

(51) Int. Cl.
*G01J 3/30* (2006.01)
*G01N 21/71* (2006.01)
*G01J 3/443* (2006.01)

(52) U.S. Cl.
CPC ............ *G01N 21/718* (2013.01); *G01J 3/443* (2013.01)

(58) Field of Classification Search
CPC .............................. G01N 21/718; G01J 3/443
USPC ........................................................ 356/318
See application file for complete search history.

(56) References Cited

U.S. PATENT DOCUMENTS

| | | | | |
|---|---|---|---|---|
| 5,751,416 A | * | 5/1998 | Singh | G01J 3/30 356/300 |
| 7,394,537 B1 | | 7/2008 | Lindfors et al. | |
| 7,999,928 B2 | | 8/2011 | Beckstead et al. | |
| 2008/0212074 A1 | * | 9/2008 | Goulter | G01J 3/02 356/51 |
| 2011/0240617 A1 | * | 10/2011 | Xu | B23K 26/00 219/121.72 |
| 2012/0033212 A1 | | 2/2012 | Barefield, II | |
| 2012/0044488 A1 | * | 2/2012 | Senac | G01J 3/02 356/316 |
| 2013/0342835 A1 | * | 12/2013 | Blacksberg | G01J 3/2803 356/301 |
| 2015/0103334 A1 | * | 4/2015 | Quant | G01N 21/718 356/51 |
| 2016/0069745 A1 | * | 3/2016 | Wang | G01J 3/443 356/318 |
| 2016/0317228 A1 | * | 11/2016 | Fermann | A61B 5/0059 |
| 2017/0045459 A1 | * | 2/2017 | Wang | G01N 21/718 |

* cited by examiner

*Primary Examiner* — Hina F Ayub

(57) ABSTRACT

This invention discloses a compact laser induced breakdown spectroscopy (LIBS) apparatus suitable for field operations. The LIBS apparatus comprises a Q-switched laser with laser pulse energy between several tens and several thousands of micro joules (µJ), which is significantly lower than that of traditional LIBS lasers. The spectrograph of the LIBS apparatus employs a dual CCD (charge coupled device) design, which maintains compact size and in the meantime offers large spectral coverage and high spectral resolution.

12 Claims, 1 Drawing Sheet

LASER INDUCED BREAKDOWN SPECTROSCOPY (LIBS) APPARATUS WITH DUAL CCD SPECTROMETER

FIELD OF THE INVENTION

This invention generally relates to a laser induced breakdown spectroscopy (LIBS) apparatus, and more specifically to a laser induced breakdown spectroscopy (LIBS) apparatus with dual CCD spectrometer.

BACKGROUND

Laser induced breakdown spectroscopy (LIBS) is a type of atomic emission spectroscopy which uses a highly energetic laser pulse as the excitation source. The laser pulse generates a high temperature micro-plasma on the surface of the sample. After this excitation, light that is characteristic of the elemental composition of the sample is emitted and analyzed within a spectrometer. LIBS has become a very popular analytical method in view of some of its unique features such as applicability to any type of sample, practically no sample preparation, remote sensing capability, and speed of analysis.

Traditional LIBS instruments utilize high power Q-switched lasers with laser pulse energy on the level of several tens or several hundreds of milli-joules (mJ). In addition, a long focal length spectrograph is generally employed to produce the required wavelength resolution. As a result, traditional LIBS instruments have large power consumption and physical dimension, which limits their capability for field operations.

SUMMARY OF THE INVENTION

It is thus the goal of the present invention to provide a compact laser induced breakdown spectroscopy (LIBS) apparatus suitable for field operations. The LIBS apparatus comprises a Q-switched laser with laser pulse energy between several tens and several thousands of micro-joules (µJ), which is significantly lower than that of traditional LIBS lasers. The spectrograph of the LIBS apparatus employs a dual CCD (charge coupled device) design, which maintains compact size and in the meantime offers large spectral coverage and high spectral resolution.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
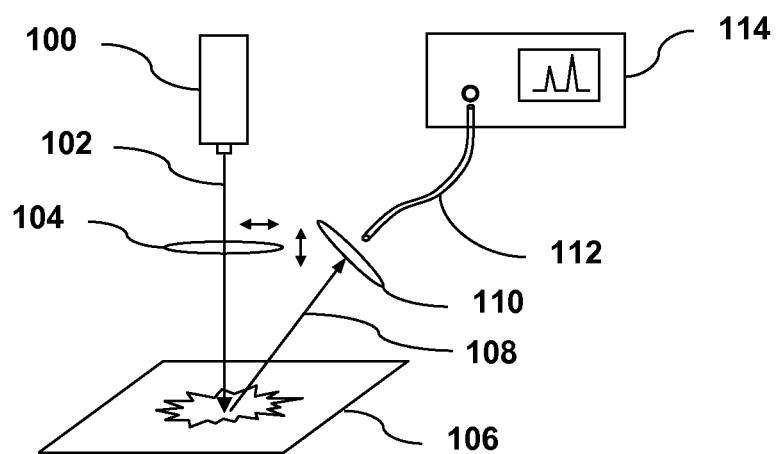
FIG. 1 illustrates an exemplary embodiment of the laser induced breakdown spectroscopy (LIBS) apparatus with dual CCD spectrometer.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a laser induced breakdown spectroscopy (LIBS) apparatus with dual CCD spectrometer. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

An exemplary embodiment of the laser induced breakdown spectroscopy (LIBS) apparatus is shown in FIG. 1. The LIBS apparatus comprises a pulsed laser 100 as the excitation light source. The pulsed laser 100 is preferably a passively Q-switched diode pumped solid state (DPSS) laser, which is capable of producing a train of laser pulses at a high repetition rate of >100 Hz, more preferably >1000 Hz (1 KHz). The pulse width of the laser is preferably less than 10 nanoseconds (ns). The laser pulse energy is preferably between several tens and several thousands of micro joules (µJ). The laser beam 102 from the pulsed laser 100 is focused by an objective lens 104 onto a surface of the sample 106. The laser pulse produces a plasma emission, i.e. LIBS signal 108 at the surface of the sample 106, which is collected by a focusing lens 110 to be focused into a light guide 112, such as an optical fiber or fiber bundle. The light guide 112 then delivers the LIBS signal 108 into an optical spectrometer device 114 for spectral analysis. In a slight variation of the LIBS apparatus, the objective lens 104 and the focusing lens 110 may be replaced with other types of optical focusing elements, such as concave mirrors, to avoid chromatic aberration of the optical lenses.

Referring back to FIG. 1, the objective lens 104 is mounted on a vibration motor (not shown) or other types of vibration device, which causes the objective lens 104 to vibrate in a direction perpendicular to the laser beam (parallel with the sample surface). The vibration pattern can be either 1-dimentional (1-D) or 2-dimentional (2-D), which results in 1-dimentional (1-D) or 2-dimentional (2-D) lateral movement of the laser beam over the sample surface. Thus the laser beam is scanned over an area of the sample surface to excite LIBS signal from multiple measurement points. The optical spectrometer device 114 operates in a continuous mode to collect the LIBS signal from all these measurement points and obtains the corresponding LIBS spectra. Additionally, the vibration motor may cause the objective lens 104 to vibrate in a direction parallel with the laser beam (vertical to the sample surface). This vibration causes the laser beam to be focused at different depths on the sample surface. Thus the laser beam can produce plasma emission from at least a portion of the measurement points even though the sample surface is uneven.

The vibration pattern of the objective lens 104 need not to be servo controlled in the present embodiment, which greatly simplifies the optical and mechanical design of the system. More preferably, the vibration pattern is random or irregular in nature with a predefined maximum vibration range, causing the laser beam to move over an entire area on the sample surface. This laser beam movement, combined with the high repetition rate of the pulsed laser 100, allows one to collect LIBS spectra from hundreds of measurement points in just a few seconds. By performing an averaging of these spectra with a processor unit, the spectral variation caused by sample non-uniformity can be greatly reduced. In comparison with the servo focusing mechanism used in conventional LIBS system, the above disclosed technique does not require any complicated feedback control, hence greatly simplifies the optical and mechanical design of the LIBS system.

By adjusting the integration time of the spectrometer device 114 to cover a plurality of periods of the laser pulse train, the spectrometer device 114 can integrate the LIBS signal produced by a plurality of laser pulses. Hence the intensity of the obtained LIBS spectrum can be greatly improved to increase the signal-to-noise ratio (SNR) of the obtained LIBS spectrum. This unique feature of the high repetition rate laser based LIBS system allows it to measure trace elements with very low concentration, hence reducing the detection limit of the LIBS system. The increased signal intensity also lessens the sensitivity requirement for the optical spectrometer device 114. In addition, the energy of individual pulses in the laser pulse train can be reduced in comparison to conventional single shot or low repetition rate laser based LIBS system to obtain the same signal level. Hence the laser pulse is less invasive to the sample.

Figure 2:
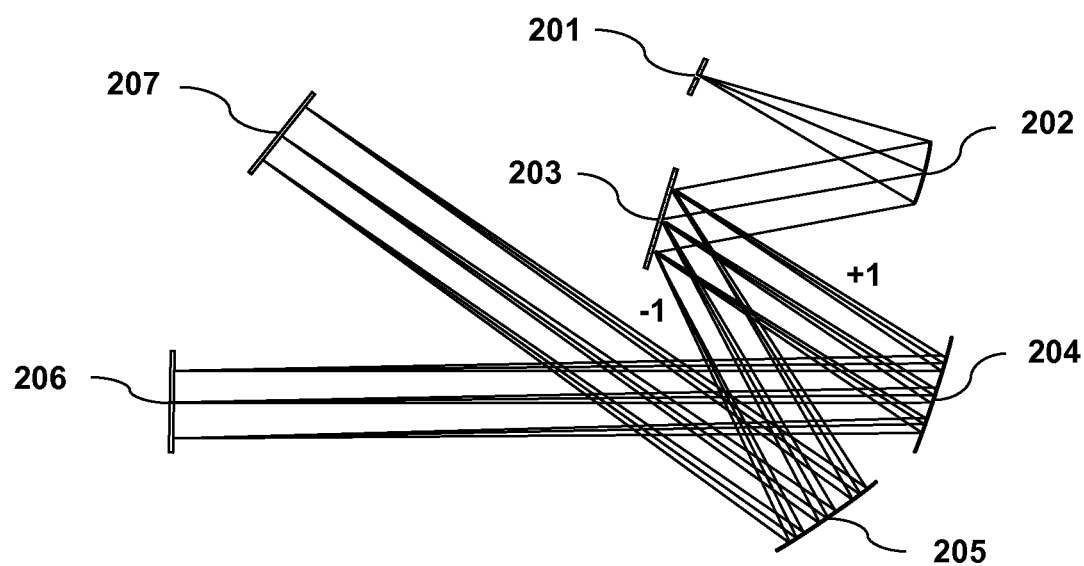
FIG. 2 is a schematic of the spectrograph design for the dual CCD spectrometer of FIG. 1.

A schematic of the spectrograph design for the spectrometer device 114 is shown in FIG. 2. In this example, the spectrometer uses two CCD (charge coupled device) arrays (or other types of detector arrays) to cover the spectral range of interest, e.g. 200-600 nm. The spectral range is divided into two spectral regions, e.g. 200-400 nm and 400-600 nm, each covered by one CCD array. The spectrograph is based on a crossed Czerny-Turner (CZ) configuration, which offers a compact and flexible spectrograph design. Referring to FIG. 2, the incident light from the entrance slit 201 is first collimated by a collimating mirror 202 and then directed towards a diffraction grating 203. The grating 203 diffracts the light into different angular directions according to the diffraction order and the wavelength of the light. In this exemplary embodiment of the spectrometer device, both the +1 and −1 diffraction order of the grating is utilized. The light in the 200-400 nm wavelength region is diffracted in the +1 diffraction order and focused by a first focusing mirror 204 to the first CCD array 206. The light in the 400-600 nm wavelength region is diffracted in the −1 diffraction order and focused by a second focusing mirror 205 to the second CCD array 207. The spectral intensity of the light is then measured by the two CCD arrays. The output from these two CCD arrays is combined to form a full spectrum of the incident light. This dual CCD spectrograph design maintains compact size of the spectrometer and in the meantime offers large spectral coverage and high spectral resolution.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A laser induced breakdown spectroscopy (LIBS) apparatus for measuring the LIBS spectrum of a subject, the LIBS apparatus comprising:
    a pulsed laser light source configured to produce a laser beam in the form of a train of laser pluses at a high repetition rate;
    an optical focusing element configured to focus the laser beam onto a surface of the subject, wherein the train of laser pulses produce a plurality of plasma emissions from the subject; and
    an optical spectrometer device operating in a continuous mode to measure an optical spectrum of the plurality of plasma emissions to obtain a LIBS spectrum;
    wherein the optical spectrometer device is set to an integration time covering a plurality of periods of the laser pulse train;
    wherein the optical spectrometer device comprises a diffract grating configured to diffract the plurality of plasma emissions in at least two diffraction orders and at least two detector arrays each configured to measure a spectral intensity of the diffracted plurality of plasma emissions in one of the at least two diffraction orders, respectively.

2. The laser induced breakdown spectroscopy (LIBS) apparatus of claim 1, wherein the pulsed laser light source has a repetition rate of greater than 100 Hz.

3. The laser induced breakdown spectroscopy (LIBS) apparatus of claim 1, wherein the pulsed laser light source has a repetition rate of greater than 1000 Hz.

4. The laser induced breakdown spectroscopy (LIBS) apparatus of claim 1, wherein the pulsed laser light source has a pulse width of less than 10 nanoseconds (ns).

5. The laser induced breakdown spectroscopy (LIBS) apparatus of claim 1, wherein the pulsed laser light source has a pulse energy of 1-10000 micro-joules (µJ).

6. The laser induced breakdown spectroscopy (LIBS) apparatus of claim 1, wherein the pulsed laser light source is a passively Q-switched diode pumped solid state (DPSS) laser.

7. The laser induced breakdown spectroscopy (LIBS) apparatus of claim 1, wherein the at least two detector arrays are CCD (charge coupled device) arrays.

8. The laser induced breakdown spectroscopy (LIBS) apparatus of claim 1, wherein the at least two diffraction orders are +1 and −1 diffraction orders.

9. The laser induced breakdown spectroscopy (LIBS) apparatus of claim 1, further comprising a vibration device configured to vibrate the optical focusing element to scan the laser beam over an area on the surface of the subject.

10. The laser induced breakdown spectroscopy (LIBS) apparatus of claim 9, wherein the vibration device produces a 1-dimentional (1-D) vibration pattern.

11. The laser induced breakdown spectroscopy (LIBS) apparatus of claim 9, wherein the vibration device produces a 2-dimentional (2-D) vibration pattern.

12. The laser induced breakdown spectroscopy (LIBS) apparatus of claim 9, wherein the vibration device produces a random vibration pattern.

\* \* \* \* \*